(12) United States Patent
Li et al.

(10) Patent No.: US 11,365,142 B2
(45) Date of Patent: Jun. 21, 2022

(54) BIOLOGICAL FILLER COMPRISING 1,5-DIHYDROXYANTHRAQUINONE AND THIOBACILLUS DENITRIFICANS POPULATION AND METHOD OF USING THE SAME FOR NITROGEN REMOVAL FROM WASTEWATER

(71) Applicant: Hebei University of Science and Technology, Shijiazhuang (CN)

(72) Inventors: Zaixing Li, Shijiazhuang (CN); Yanfang Liu, Shijiazhuang (CN); Xiaoshuai Liu, Shijiazhuang (CN); Xin Yue, Shijiazhuang (CN); Jianwei Lyu, Shijiazhuang (CN); Yongtao Lyu, Shijiazhuang (CN); Fan Zhang, Shijiazhuang (CN); Xuebin Han, Shijiazhuang (CN)

(73) Assignee: HEBEI UNIVERSITY OF SCIENCE AND TECHNOLOGY, Shijiazhuang (CN)

( * ) Notice: Subject to any disclaimer, the term of this patent is extended or adjusted under 35 U.S.C. 154(b) by 0 days.

(21) Appl. No.: 17/109,094

(22) Filed: Dec. 1, 2020

(65) Prior Publication Data
US 2022/0048800 A1 Feb. 17, 2022

(30) Foreign Application Priority Data
Aug. 17, 2020 (CN) .......................... 202010827670.6

(51) Int. Cl.
*C02F 3/34* (2006.01)
*C02F 3/30* (2006.01)
*C02F 3/32* (2006.01)
*C12N 11/08* (2020.01)
*C02F 101/16* (2006.01)
*C02F 3/00* (2006.01)
*C12N 11/084* (2020.01)

(52) U.S. Cl.
CPC .............. *C02F 3/348* (2013.01); *C02F 3/305* (2013.01); *C02F 3/327* (2013.01); *C02F 3/341* (2013.01); *C02F 2003/001* (2013.01); *C02F 2101/163* (2013.01); *C02F 2203/00* (2013.01); *C12N 11/084* (2020.01)

(58) Field of Classification Search
CPC .......... C02F 3/348; C02F 3/305; C02F 3/327; C02F 3/341; C02F 2003/001; C02F 2101/163; C02F 2203/00; C12N 11/084
USPC ........ 210/605, 615, 616, 617, 903; 435/174, 435/176, 177, 180
See application file for complete search history.

(56) References Cited

U.S. PATENT DOCUMENTS

| 6,808,622 | B2 * | 10/2004 | Okamoto | .............. C02F 3/1273 210/151 |
| 9,994,466 | B2 * | 6/2018 | Dove | ........................ C02F 9/00 |
| 2006/0257662 | A1 * | 11/2006 | Bujard | .................. C09C 1/0018 428/404 |

(Continued)

*Primary Examiner* — Fred Prince
(74) *Attorney, Agent, or Firm* — Matthias Scholl P.C.; Matthias Scholl (57) ABSTRACT

A biological filler includes an embedding agent and an embedded complex. The embedded complex includes a scallop shell powder, 1,5-dihydroxyanthraquinone, and *Thiobacillus denitrificans*. The embedding agent includes a poly(vinyl alcohol)-sodium alginate blend membrane and a crosslinked composite membrane. The embedded complex is embedded by the embedded agent.

11 Claims, 4 Drawing Sheets

(56) References Cited

U.S. PATENT DOCUMENTS

2014/0370578 A1* 12/2014 Hao .................... B01D 53/228
  435/266
2015/0125901 A1* 5/2015 Razavi-Shirazi ....... C02F 3/105
  435/42

* cited by examiner

BIOLOGICAL FILLER COMPRISING 1,5-DIHYDROXYANTHRAQUINONE AND THIOBACILLUS DENITRIFICANS POPULATION AND METHOD OF USING THE SAME FOR NITROGEN REMOVAL FROM WASTEWATER

CROSS-REFERENCE TO RELATED APPLICATIONS

Pursuant to 35 U.S.C. § 119 and the Paris Convention Treaty, this application claims foreign priority to Chinese Patent Application No. 202010827670.6 filed on Aug. 17, 2020, the contents of all of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a biological filler comprising 1,5-dihydroxyanthraquinone and *Thiobacillus denitrificans* population and a method of using the same for nitrogen removal from wastewater.

In the process of sulfur-based autotrophic denitrification, under anoxic conditions, *Thiobacillus denitrificans* employ elemental sulfur as electron donor and $NO_3$—N as electron acceptor to denitrify wastewater. However, the following disadvantages are associated with the sulfur-based autotrophic denitrification technology: low efficiency, easy loss of bacteria, and susceptibility to temperature and pH.

Microbial embedding and immobilization technology is also used for wastewater treatment. However, the traditional embedding method employs sodium alginate as an embedding agent, which has the disadvantages of low mechanical strength, poor degradation resistance, and large void size of gel network. As for embedding through polyvinyl alcohol (PVA), the embedding agent is adhesive and difficult to form, and has large water swelling in practical use, thus weakening the strength of embedded carriers over time and destroying the embedding.

Certain quinone compounds can accelerate the degradation of some pollutants. For example, 1,5-dichloroanthraquinone or 1,8-dichloroanthraquinone is embedded with microbes for denitrification of azo dyes and nitroaromatic compounds. There are still some problems in practical application, such as low mass transfer rate, low nitrogen removal efficiency and so on.

SUMMARY

To solve the above problems, the disclosure provides a biological filler comprising 1,5-dihydroxyanthraquinone, *Thiobacillus denitrificans* and a scallop shell powder. The scallop shell powder is cheap and biocompatible. The microorganisms of the biological filler are not easy to lose. The biological filler can improve the mass transfer rate and denitrification rate and denitrification conversion rate in the process of wastewater treatment.

Specifically, in one aspect, the disclosure provides a biological filler, comprising an embedding agent and an embedded complex; the embedded complex comprises a scallop shell powder, 1,5-dihydroxyanthraquinone, and *Thiobacillus denitrificans*; the embedding agent comprises a poly(vinyl alcohol)-sodium alginate blend membrane and a crosslinked composite membrane; and the embedded complex is embedded by the embedded agent.

In another aspect, the disclosure provides a method for preparing a biological filler, the method comprising:
1) preparing *Thiobacillus denitrificans* population and a scallop shell powder; and mixing poly(vinyl alcohol), sodium alginate and water and cooling to yield a precursor of an embedding agent;
2) uniformly mixing the scallop shell powder, 1,5-dihydroxyanthraquinone, and the *Thiobacillus denitrificans* population, to yield an embedded complex;
3) uniformly mixing the precursor of an embedding agent and the embedded complex; adding dropwise a mixture comprising the precursor and the embedded complex to a crosslinker solution, thereby yielding immobilized microspheres; and
4) freezing the immobilized microspheres, thawing and air drying, thereby yielding a biological filler comprising 1,5-dihydroxyanthraquinone and *Thiobacillus denitrificans* population.

In a class of this embodiment, in 1), the *Thiobacillus denitrificans* population is prepared as follows: preparing a liquid medium comprising 0.02-0.025 mol/L of sodium thiosulfate, 0.018-0.022 mol/L of potassium nitrate, 0.01-0.15 mol/L of sodium bicarbonate, 0.007-0.008 mol/L of potassium dihydrogen phosphate, and 0.002-0.0028 mol/L magnesium chloride hexahydrate, sterilizing the liquid medium, and the liquid medium having a pH value of 6.8-7.2; culturing *Thiobacillus denitrificans* in the liquid medium; collecting a bacterial fluid of *Thiobacillus denitrificans*, centrifuging the bacterial fluid.

In a class of this embodiment, the *Thiobacillus denitrificans* is cultured in the liquid medium at 28-32° C. for 18-24 hours; and the bacterial fluid is centrifuged at 3000-4000 rpm for 5-8 min.

In a class of this embodiment, in 1), the scallop shell powder is purchased from market or is prepared as follows: washing scallop shells in water, drying the scallop, washing the scallop with hydrochloric acid, grinding the scallop using a 45-60 mesh sieve, drying and sterilizing a resulting powder. Specifically, the resulting powder is sterilized using an ultraviolet lamp or ozone.

In a class of this embodiment, the scallop is washed with 3-5 wt. % of hydrochloric acid for 2-3 min and dried at 120-160° C.

In a class of this embodiment, in 1), the precursor of the embedding agent is prepared as follows: adding poly(vinyl alcohol) and sodium alginate to water, heating a mixture of the poly(vinyl alcohol), the sodium alginate and the water to 95-99° C. (in this temperature, poly(vinyl alcohol) and sodium alginate are easily dissolved in water) and a viscous liquid is formed; cooling to 20-26° C. and sterilizing the viscous liquid. Optionally, the mixture of poly(vinyl alcohol), sodium alginate and water are heated in a water bath, and the viscous liquid is sterilized under high temperature or an ultraviolet lamp.

In a class of this embodiment, the poly(vinyl alcohol) accounts for 7.5-10 wt. % of the precursor, and the sodium alginate accounts for 0.8-3 wt. % of the precursor.

In a class of this embodiment, in 2), a mass ratio of the scallop shell powder to the *Thiobacillus denitrificans* population is between 8:1 and 10:1; the *Thiobacillus denitrificans* population is stirred, adsorbed, and diffused on the scallop shell powder; and the 1,5-dihydroxyanthraquinone accounts for 2.5-3.5 wt. % of the embedded complex, particularly, 3 wt. %.

In a class of this embodiment, in 2), the scallop shell powder, 1,5-dihydroxyanthraquinone, and the *Thiobacillus denitrificans* population are uniformly mixed for 10-20 min to yield the embedded complex.

In a class of this embodiment, in 3), the mixture comprising the precursor and the embedded complex is added dropwise to a crosslinker solution using a needle tube; the immobilized microspheres have a diameter of 3-4 mm; the crosslinker solution is an aqueous solution comprising calcium chloride and saturated boric acid; and a concentration of calcium chloride is 2-5 wt. %.

In a class of this embodiment, in 4), the immobilized microspheres are washed using deionized water, frozen at −20° C., thawed and dried in air twice, and thawed at room temperature, to yield the biological filler comprising 1,5-dihydroxyanthraquinone and *Thiobacillus denitrificans* population.

In a class of this embodiment, the immobilized microspheres are frozen at −20° C. for 12-24 hours, and thawed at 0-3° C.

The disclosure also provides a method of nitrogen removal from wastewater by denitrification, the method comprising treating wastewater containing nitrate nitrogen in an upflow fixed-bed reactor comprising a reaction zone filled with the biological filler.

In a class of this embodiment, the upflow fixed-bed reactor comprises a column reaction tower comprising a water inlet disposed on a lower part of the column reaction tower and a water outlet disposed on an upper part of the column reaction tower; the column reaction tower further comprises, from bottom to top, a porous supporting plate, a pebble bearing layer, and the reaction zone; the reaction zone is filled with the biological filler and a sulfur-dolomite composite filler; when in use, the wastewater containing nitrate nitrogen is introduced to the column reaction tower via the water inlet, distributed via the porous supporting plate, flows through the pebble bearing layer and rises to the reaction zone, where the wastewater is denitrified by the *Thiobacillus denitrificans*, and treated water flows out of the column reaction tower via the water outlet.

The hydraulic retention time (HRT) of an influent in the upflow fixed-bed reactor is 3-5 hours, which can improve the nitrate removal efficiency. With the improvement of nitrate removal efficiency, the hydraulic retention time of the subsequent influent can be shortened.

In a class of this embodiment, a temperature of the reaction zone is 29.8-31° C.; the pH of the wastewater is 7-7.5 and has a dissolved oxygen less than 0.5 mg/L.

In a class of this embodiment, in the sulfur-dolomite composite filler, the particle size of sulfur and dolomite is 5-10 mm, and the volume ratio of the sulfur to the dolomite is between 3:1 and 4:1.

In a class of this embodiment, when the C/N of the nitrate wastewater is between 3:1 and 7:1, the addition amount of the biological filler accounts for ⅓-½ of the volume of the reaction zone.

The following advantages are associated with the biological filler of the disclosure.

1. 1,5-dihydroxyanthraquinone in the biological filler functions as a redox mediator, which can effectively promote the rate of autotrophic denitrification, shorten the hydraulic retention time, and reduce the cost of wastewater treatment.

2. The scallop shell powder is cheap and biocompatible, can effectively diffuse 1,5-dihydroxyanthraquinone and *Thiobacillus denitrificans*, preventing the loss of *Thiobacillus denitrificans*, and maintaining the wastewater treatment capacity of the biological filler.

3. The embedding agent comprising polyvinyl alcohol and sodium alginate hydrogel is elastic, flexible and hydrous, thus preventing the adhesion and spheroidization which tend to occur when poly(vinyl alcohol) is used alone.

4. The scallop shell powder is hydrophilic and biocompatible, which can accumulate *Thiobacillus denitrificans* and increase its concentration. The scallop shell powder contains trace elements and amino acids (nutrients) needed for the growth of *Thiobacillus denitrificans*, and $CaCO_3$ functioning to neutralize the acid produced by autotrophic reaction.

5. The method of nitrogen removal from wastewater using the biological filler features quick response time and short hydraulic retention time.

DETAILED DESCRIPTION

To further illustrate, embodiments detailing a biological filler and a method for preparing the same are described below. It should be noted that the following embodiments are intended to describe and not to limit the disclosure.

Figure 1:
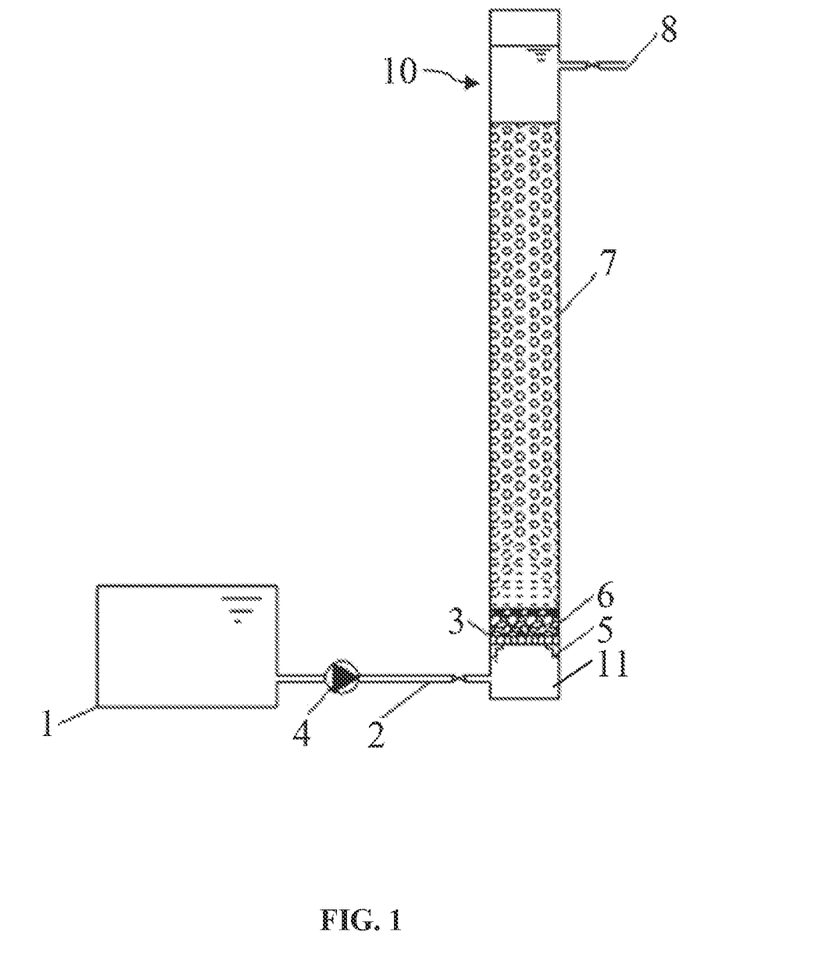
FIG. 1 is a schematic diagram of an upflow fixed-bed reactor involved in a method of nitrogen removal from wastewater in accordance with one embodiment of the disclosure.

As shown in FIG. 1, provided is an upflow fixed-bed reactor for nitrogen removal from nitrate wastewater. The upflow fixed-bed reactor is filled with a biological filler comprising *Thiobacillus denitrificans*. The upflow fixed-bed reactor comprises a column reaction tower 10. In certain embodiments, the column reaction tower has a height of 1 m and an inner diameter of 100 mm, and is made of organic glass.

The column reaction tower 10 comprises a water inlet 2, a water outlet 8, a water distribution zone 11, and an L-shaped support member 5. The column reaction tower 10 further comprises a lower part, an upper part, and an inner wall. The water inlet 2 is disposed on the lower part and the water outlet 8 is disposed on the lower part. The water distribution zone 11 is connected to the water inlet 2. The L-shaped support member 5 is disposed on the inner wall. The column reaction tower 10 further comprises, from bottom to top, a porous supporting plate 3, a pebble bearing layer 6, and a reaction zone 7. The L-shaped support member 5 is configured to support the porous supporting plate 3. The porous supporting plate 3 comprises a plurality of through holes configured to distribute the water throughout the porous supporting plate 3. The pebble bearing layer 6 is disposed between the porous supporting plate 3 and the reaction zone 7. The reaction zone 7 is filled with the biological filler and a sulfur-dolomite composite filler.

The sulfur-dolomite composite filler comprises sulfur and dolomite. The particle size of sulfur and dolomite is 5-10 mm, and the volume ratio of the sulfur to the dolomite is between 3:1 and 4:1 (in the following examples and comparative examples, the volume ratio of the sulfur to the dolomite is 3:1).

The biological filler comprises an embedding agent and an embedded complex. The embedded complex comprises a scallop shell powder, 1,5-dihydroxyanthraquinone, and *Thiobacillus denitrificans*. The embedding agent comprises a poly(vinyl alcohol)-sodium alginate blend membrane and a crosslinked composite membrane. The embedded complex is embedded by the embedded agent. The optimal addition amount of the biological filler has a certain degree of correlation with C/N value. When the C/N value of the nitrate wastewater is low (ranging from 3-7.1), the addition amount of the biological filler accounts for ⅓-½ of the volume of the reaction zone. In Examples and Comparative Examples, the addition amount of the biological filler accounts for ⅓ of the reaction zone 7.

The column reaction tower 10 is connected to a wastewater storage tank 1 configured to balance the amount of water and adjust the pH of wastewater. To further enhance the effect of sulfur-based autotrophic denitrification, the temperature of the reaction zone 7 is 29.8-31° C.; the pH of wastewater is adjusted to 7-7.5; and the concentration of oxygen dissolved (OD) is adjusted to <0.5 mg/L. The column reaction tower 10 is connected to the wastewater storage tank 1 through a peristaltic pump 4. The operating parameters of the peristaltic pump 4 are adjusted to adjust the velocity and hydraulic residence time of the wastewater entering the column reaction tower 10.

When in use, the wastewater containing nitrate nitrogen is introduced into the column reaction tower 10 via the water inlet 2, is distributed via the porous supporting plate 3, flows through the pebble bearing layer 6, rises in the reaction zone 7, where the wastewater is denitrified by the *Thiobacillus denitrificans*, and treated water flows out of the column reaction tower via the water outlet 8.

The reaction zone 7 is filled with the biological filler and the sulfur-dolomite composite filler, so as to provide advantages in fast start-up and enhanced denitrification effect over prior art upflow fixed-bed reactors. When in use, the nitrate-containing wastewater is introduced into the upflow fixed-bed reactor. The velocity of the wastewater is adjusted through the peristaltic pump 4 to control the hydraulic residence time of the nitrate-containing wastewater. The hydraulic retention time of an influent in the upflow fixed-bed reactor is 3-5 hours, which can improve the nitrate removal efficiency. With the improvement of nitrate removal efficiency, the hydraulic retention time of the subsequent influent can be shortened.

Different biological fillers filled in the reaction zone 7 are tested for their ability to treat the wastewater containing nitrate nitrogen.

Example 1

A biological filler was prepared as follows:
1) *Thiobacillus denitrificans* were inoculated in a liquid medium, cultured at 28° C. for 18 hours, and centrifuged at 3000 rpm/min for 8 min, yielding a viscous liquid;
the liquid medium was prepared as follows: 5.0 g of sodium thiosulfate pentahydrate, 2.0 g of potassium nitrate, 1.0 g of sodium bicarbonate, 1.0 g of potassium dihydrogen phosphate, and 0.5 g of hexahydrate were dissolved in 1000 mL of deionized water; the pH of the mixture was adjusted to 7.0 with sodium hydroxide; the mixture was sterilized at 121° C. for 30 min to form a liquid medium; the *Thiobacillus denitrificans* were inoculated at an initial concentration of OD600=0.5; the liquid medium was employed in the following examples and comparative examples;

2) the poly(vinyl alcohol) and the sodium alginate were added to the water and heated to 99° C. to form a viscous liquid; the viscous liquid was cooled to 25° C. and sterilized to yield a precursor of an embedding agent; the poly(vinyl alcohol) accounted for 7.5 wt. % of the precursor, and the sodium alginate accounted for 0.8 wt. % of the precursor;

3) a scallop was washed in water, dried, washed at 95° C. for 2 min with 3% hydrochloric acid by mass, and ground using a 45 mesh sieve; the scallop shell powder was dried in an oven at 125° C., cooled to the temperature, spread on a filter paper, irradiated by using a UV lamp for 25 min, and sterilized;

4) the scallop shell powder was mixed with the viscous liquid in 1) in a mass ratio of 8:1; 1,5-dihydroxyanthraquinone accounting for 3.0 wt. % of the embedded complex was added to the mixture, uniformly stirred, and adsorbed for 10 min to diffuse the viscous liquid on the scallop shell powder, thereby yielding an embedded complex;

5) the precursor in 2) was uniformly mixed with the embedded complex in 4); the mixture was added dropwise to a crosslinker solution using a needle tube to yield an immobilized microspheres having a diameter of 3-4 mm; the crosslinker solution was an aqueous solution comprising calcium chloride and saturated boric acid; and a concentration of the calcium chloride was 2-5 wt. %; and 6) the immobilized microspheres were washed several times using deionized water, frozen at −20° C. four 20 hours, thawed and dried in air once, and thawed at room temperature, thereby yielding a biological filler comprising 1,5-dihydroxyanthraquinone and *Thiobacillus denitrificans* population;

The biological filler was filled in the reaction zone 7.

Comparative Example 1

Comparative Example 1 was performed in the same manner as Example 1, except that the scallop shell powder was mixed with the viscous liquid in a mass ratio of 8:1, and directly filled in the reaction zone 7.

Comparative Example 2

Comparative Example 2 was performed in the same manner as Example 1, except that no 1,5 dihydroxyanthraquinone was added. The resulting biological filler was filled in the reaction zone 7.

Comparative Example 3

Comparative Example 3 was performed in the same manner as Example 1, except that the scallop shell powder was replaced with the same amount of calcium carbonate powder. The resulting biological filler was filled in the reaction zone 7.

Example 2

A biological filler was prepared as follows:

1) *Thiobacillus denitrificans* were inoculated in a liquid medium, cultured at 31° C. for 20 hours, and centrifuged at 3000 rpm/min for 8 min, yielding a viscous liquid;

2) the poly(vinyl alcohol) and the sodium alginate were added to the water and heated to 99° C. to form a viscous liquid; the viscous liquid was cooled to 25° C. and sterilized to yield a precursor of an embedding agent; the poly(vinyl alcohol) accounted for 8.0 wt. % of the precursor, and the sodium alginate accounted for 2.0 wt. % of the precursor;

3) a scallop was washed in water, dried, washed at 95° C. for 2 min with 4% hydrochloric acid by mass, and ground using a 50 mesh sieve; the scallop shell powder was dried in an oven at 125° C., cooled to the temperature, spread on a filter paper, irradiated by using a UV lamp for 25 min, and sterilized;

4) the scallop shell powder was mixed with the viscous liquid in 1) in a mass ratio of 9:1; 1,5-dihydroxyanthraquinone accounting for 3.0 wt. % of the embedded complex was added to the mixture, uniformly stirred, and adsorbed for 10 min to diffuse the viscous liquid on the scallop shell powder, thereby yielding an embedded complex;

5) the precursor in 2) was uniformly mixed with the embedded complex in 4); the mixture was added dropwise to a crosslinker solution using a needle tube to yield an immobilized microspheres having a diameter of 3-4 mm; the crosslinker solution was an aqueous solution comprising calcium chloride and saturated boric acid; and a concentration of the calcium chloride was 3.0 wt. %; and 6) the immobilized microspheres were washed several times using deionized water, frozen at −20° C. for 20 hours, thawed and dried in air once, and thawed at room temperature, thereby yielding a biological filler comprising 1,5-dihydroxyanthraquinone and *Thiobacillus denitrificans* population.

The biological filler was filled in the reaction zone 7.

Comparative Example 4

Comparative Example 1 was performed in the same manner as Example 2, except that the scallop shell powder was mixed with the viscous liquid in a mass ratio of 9:1, and directly filled in the reaction zone 7.

Comparative Example 5

Comparative Example 1 was performed in the same manner as Example 2, except that no 1,5 dihydroxyanthraquinone was added. The resulting biological filler was filled in the reaction zone 7.

Example 3

A biological filler was prepared as follows:

1) *Thiobacillus denitrificans* were inoculated in a liquid medium, cultured at 30° C. for 24 hours, and centrifuged at 3000 rpm/min for 8 min, yielding a viscous liquid;

2) the poly(vinyl alcohol) and the sodium alginate were added to the water and heated to 99° C. to form a viscous liquid; the viscous liquid was cooled to 25° C. and sterilized to yield a precursor of an embedding agent; the poly(vinyl alcohol) accounted for 9.0 wt. % of the precursor, and the sodium alginate accounted for 3.0 wt. % of the precursor;

3) a scallop was washed in water, dried, washed at 95° C. for 2 min with 4% hydrochloric acid by mass, and ground using a 60 mesh sieve; the scallop shell powder was dried in an oven at 125° C., cooled to the temperature, spread on a filter paper, irradiated by using a UV lamp for 25 min, and sterilized;

4) the scallop shell powder was mixed with the viscous liquid in 1) in a mass ratio of 10:1; 1,5-dihydroxyanthraquinone accounting for 3.0 wt. % of the embedded complex was added to the mixture, uniformly stirred, and adsorbed for 10 min to diffuse the viscous liquid on the scallop shell powder, thereby yielding an embedded complex;

5) the precursor in 2) was uniformly mixed with the embedded complex in 4); the mixture was added dropwise to a crosslinker solution using a needle tube to yield an immobilized microspheres having a diameter of 3-4 mm; the crosslinker solution was an aqueous solution comprising calcium chloride and saturated boric acid; and a concentration of the calcium chloride was 4.0 wt. %; and 6) the immobilized microspheres were washed several times using deionized water, frozen at −20° C. for 20 hours, thawed and dried in air twice, and thawed at room temperature, thereby yielding a biological filler comprising 1,5-dihydroxyanthraquinone and *Thiobacillus denitrificans* population.

The biological filler was filled in the reaction zone 7.

Comparative Example 6

Comparative Example 1 was performed in the same manner as Example 3, except that the scallop shell powder was mixed with the viscous liquid in a mass ratio of 10:1, and directly filled in the reaction zone 7.

Comparative Example 7

Comparative Example 2 was performed in the same manner as Example 3, except that no 1,5 dihydroxyanthraquinone was added. The resulting biological filler was filled in the reaction zone 7.

The biological fillers prepared in Examples 1-3 were respectively filled in the reaction zone 7. The addition amount of each biological filler accounted for ⅓ of the volume of the reaction zone, and ⅔ of the volume of the reaction zone 7 was filled with the sulfur-dolomite composite filler (which mainly provides electron donors for autotrophic denitrification). The volume ratio of sulfur to dolomite was 3:1. The volume of the reaction zone 7 was 5 L. 10 upflow fixed-bed reactors were employed for testing.

A simulated wastewater containing nitrate nitrogen was used as a test water. The test water was prepared as follows: 0.2 g of $KNO_3$, 0.2 of $KH_2PO_4$, 1.25 g of $NaHCO_3$, and 55.5 mg/L of the nitrate nitrogen were dissolved in ultrapure water; the resulting solution was transferred to a 1 L volumetric flask, and diluted to the mark with ultrapure water. The test water was introduced into the upflow fixed-bed reactor via the water inlet 2. The temperature of the reaction zone was 29.8-31° C. for 72 hours. The treated water was sampled every 12 hours, filtered with filter paper, and measured for the concentration of nitrate. The experimental results were shown in FIGS. 1, 2, and 3.

Figure 2:
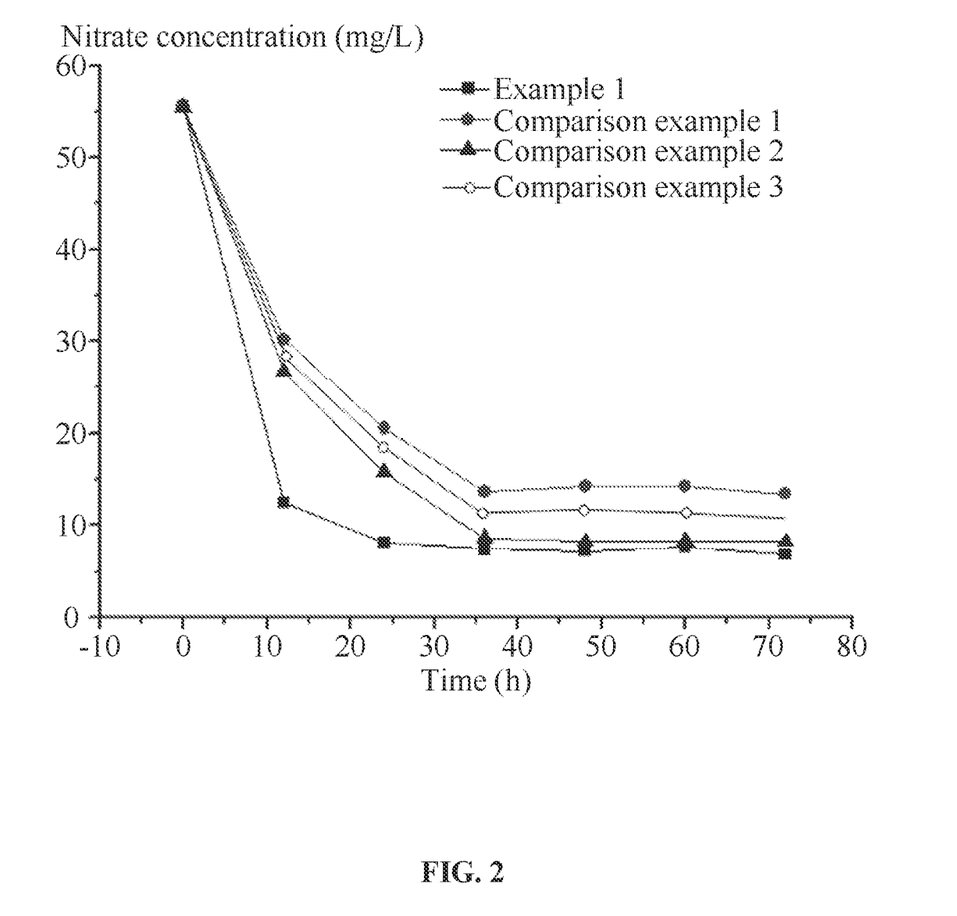
FIG. 2 shows change curves of nitrate nitrogen removal rate in simulated ammonia nitrogen wastewater over time when a biological filler prepared in Example 1 and Comparison Examples 1-3 is loaded into an upflow fixed bed reactor for wastewater treatment.
Figure 3:
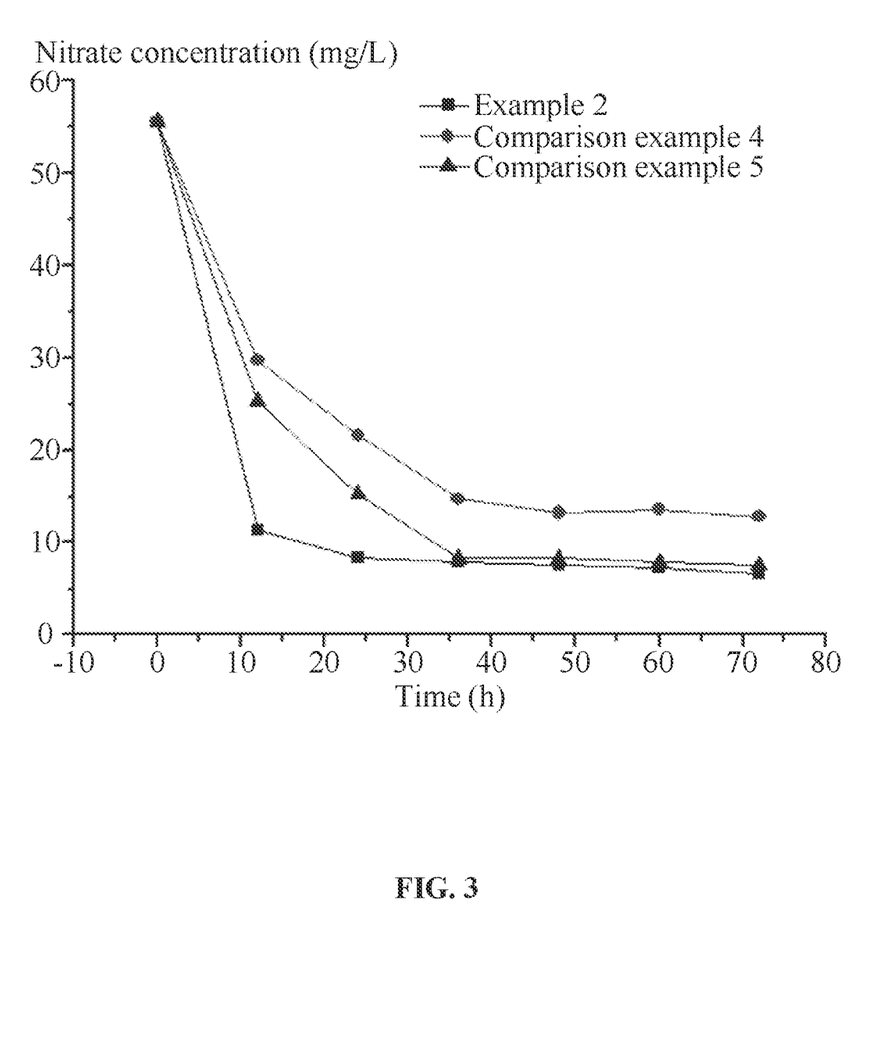
FIG. 3 shows change curves of nitrate nitrogen removal rate in simulated ammonia nitrogen wastewater over time when a biological filler prepared in Example 2 and Comparison Examples 4-5 is loaded into an upflow fixed bed reactor for wastewater treatment.
Figure 4:
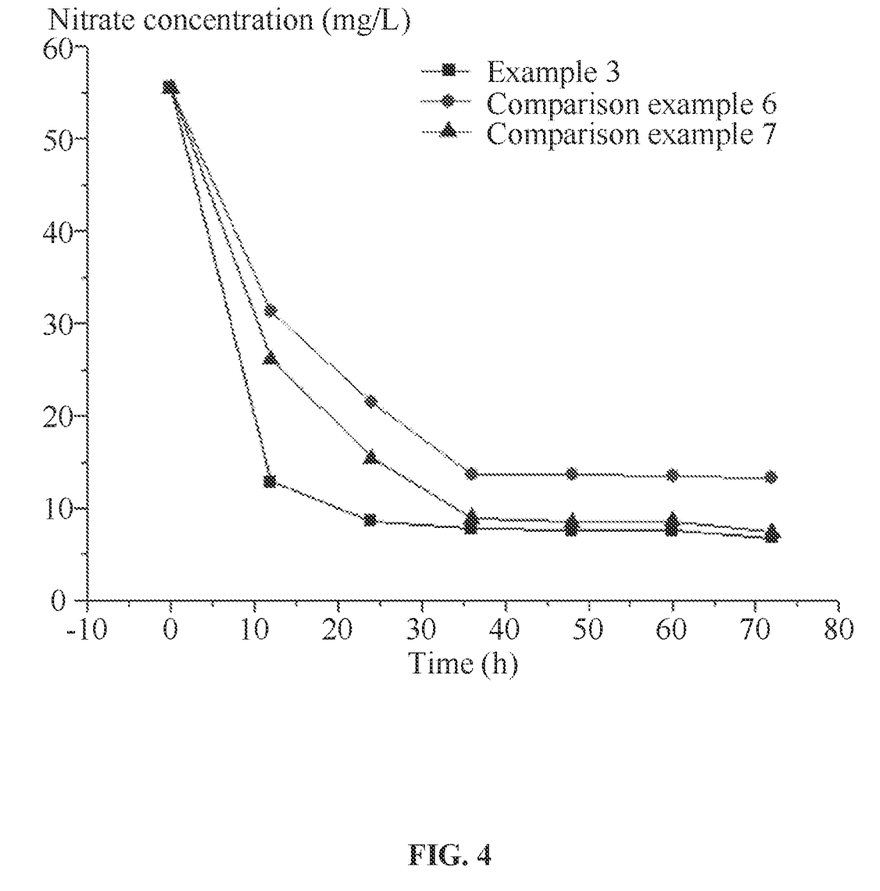
FIG. 4 shows change curves of nitrate nitrogen removal rate in simulated ammonia nitrogen wastewater over time when a biological filler prepared in Example 3 and Comparison Examples 6-7 is loaded into an upflow fixed bed reactor for wastewater treatment.

Referring to FIGS. 2-4, the biological fillers prepared in Examples 1-3 was filled in the upflow fixed-bed reactor and the reaction was performed under the corresponding conditions for 48 hours. The concentration of the nitrate nitrogen in the treated water respectively stabilized at 7.2 mg/L, 7.6 mg/L, and 7.1 mg/L, respectively. The removal rate of nitrate nitrogen in the treated water was 87.03%, 86.31% and 87.21%, respectively. The removal rate of nitrate nitrogen in Example 1 was substantially higher than that in Comparative Example 3 during the reaction period of 12 h to 72 h.

After reaction for 24 hours, the removal rate of nitrate nitrogen in the examples 1-3 were respectively increased by 12.80%, 10.10% and 11.71% compared with the Comparative Examples 1, 4 and 6. No 1,5-dihydroxyanthraquinone was involved in the Comparative Examples 1, 4 and 6.

After reaction for 12 hours, the removal rate of nitrate nitrogen in the examples 1-3 was more than twice that of the Comparative Examples 2, 5 and 7. No 1,5-dihydroxyanthraquinone was involved in the Comparative Examples 2, 5 and 7 while the immobilization process was performed.

The experiment results indicate that the biological filler of the disclosure effectively increase the rate of sulfur-based autotrophic denitrification and the denitrification conversion rate, shorten the hydraulic retention time, and has practical application in engineering.

It will be obvious to those skilled in the art that changes and modifications may be made, and therefore, the aim in the appended claims is to cover all such changes and modifications.

What is claimed is:

1. A biological filler, comprising an embedding agent and an embedded complex; wherein the embedded complex comprises a scallop shell powder, 1,5-dihydroxyanthraquinone, and *Thiobacillus denitrificans*; the embedding agent comprises a poly(vinyl alcohol)-sodium alginate blend membrane and a crosslinked composite membrane; and the embedded complex is embedded by the embedding agent.

2. A method for preparing a biological filler, the method comprising:
   1) preparing *Thiobacillus denitrificans* population and a scallop shell powder; and mixing poly(vinyl alcohol), sodium alginate and water and cooling to yield a precursor of an embedding agent;
   2) uniformly mixing the scallop shell powder, 1,5-dihydroxyanthraquinone, and the *Thiobacillus denitrificans* population, to yield an embedded complex;
   3) uniformly mixing the precursor of an embedding agent and the embedded complex; adding dropwise a mixture comprising the precursor and the embedded complex to a crosslinker solution, thereby yielding immobilized microspheres; and
   4) freezing the immobilized microspheres, thawing and air drying, thereby yielding a biological filler comprising 1,5-dihydroxyanthraquinone and *Thiobacillus denitrificans* population.

3. The method of claim 2, wherein in 1), the *Thiobacillus denitrificans* population is prepared as follows: preparing a liquid medium comprising 0.02-0.025 mol/L of sodium thiosulfate, 0.018-0.022 mol/L of potassium nitrate, 0.01-0.15 mol/L of sodium bicarbonate, 0.007-0.008 mol/L of potassium dihydrogen phosphate, and 0.002-0.0028 mol/L magnesium chloride hexahydrate, sterilizing the liquid medium, and the liquid medium having a pH value of 6.8-7.2; culturing *Thiobacillus denitrificans* in the liquid medium; collecting a bacterial fluid of *Thiobacillus denitrificans*, centrifuging the bacterial fluid.

4. The method of claim 2, wherein in 1), the scallop shell powder is prepared as follows: washing scallop shells in water, drying the scallop, washing the scallop with hydrochloric acid, grinding the scallop using a 45-60 mesh sieve, drying and sterilizing a resulting powder.

5. The method of claim 2, wherein in 1), the precursor of an embedding agent is prepared as follows: adding poly (vinyl alcohol) and sodium alginate to water, heating a mixture of the poly(vinyl alcohol), the sodium alginate and the water to 95-99° C. and a viscous liquid is formed; cooling to 20-26° C. and sterilizing the viscous liquid; the poly(vinyl alcohol) accounts for 7.5-10 wt. % of the precursor, and the sodium alginate accounts for 0.8-3 wt. % of the precursor.

6. The method of claim 3, wherein in 2), a mass ratio of the scallop shell powder to the *Thiobacillus denitrificans* population is between 8:1 and 10:1; the *Thiobacillus denitrificans* population is stirred, adsorbed, and diffused on the scallop shell powder; and the 1,5-dihydroxyanthraquinone accounts for 2.5-3.5 wt. % of the embedded complex.

7. The method of claim 2, wherein in 3), the mixture comprising the precursor and the embedded complex is added dropwise to a crosslinker solution using a needle tube; the immobilized microspheres have a diameter of 3-4 mm; the crosslinker solution is an aqueous solution comprising calcium chloride and saturated boric acid; and a concentration of the calcium chloride is 2-5 wt. %.

8. The method of claim 2, wherein in 4), the immobilized microspheres are washed using deionized water, frozen at −20° C., thawed and dried in air twice, and thawed at room temperature, to yield the biological filler comprising 1,5-dihydroxyanthraquinone and *Thiobacillus denitrificans* population.

9. The method of claim 8, wherein the immobilized microspheres are frozen at −20° C. for 12-24 hours, and thawed at 0-3° C.

10. A method of nitrogen removal from wastewater by denitrification, the method comprising treating wastewater containing nitrate nitrogen in an upflow fixed-bed reactor comprising a reaction zone filled with the biological filler of claim 1.

11. The method of claim 10, wherein the upflow fixed-bed reactor comprises a column reaction tower comprising a water inlet disposed on a lower part of the column reaction tower and a water outlet disposed on an upper part of the column reaction tower; the column reaction tower further comprises, from bottom to top, a porous supporting plate, a pebble bearing layer, and the reaction zone; the reaction zone is filled with the biological filler and a sulfur-dolomite composite filler; when in use, the wastewater containing nitrate nitrogen is introduced to the column reaction tower via the water inlet, distributed via the porous supporting plate, flows through the pebble bearing layer and rises to the reaction zone, where the wastewater is denitrified by the *Thiobacillus denitrificans*, and treated water flows out of the column reaction tower via the water outlet.

* * * * *